(12) United States Patent
Volpe et al.

(10) Patent No.: US 10,321,877 B2
(45) Date of Patent: Jun. 18, 2019

(54) MEDICAL DEVICE WITH ACOUSTIC SENSOR

(71) Applicant: ZOLL Medical Corporation, Chelmsford, MA (US)

(72) Inventors: Shane S. Volpe, Saltsburg, PA (US); Gregory R. Frank, Mt. Lebanon, PA (US); Thomas E. Kaib, North Huntingdon, PA (US); Steven J. Szymkiewicz, Bethel Park, PA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 293 days.

(21) Appl. No.: 15/074,020

(22) Filed: Mar. 18, 2016

(65) Prior Publication Data
US 2016/0270738 A1    Sep. 22, 2016

Related U.S. Application Data

(60) Provisional application No. 62/134,881, filed on Mar. 18, 2015.

(51) Int. Cl.
*A61B 7/04*    (2006.01)
*A61B 5/0205*    (2006.01)
(Continued)

(52) U.S. Cl.
CPC .......... *A61B 5/7278* (2013.01); *A61B 5/0408* (2013.01); *A61B 5/08* (2013.01);
(Continued)

(58) Field of Classification Search
CPC ....... A61B 5/11; A61B 5/1118; A61B 5/4815; A61B 5/681; A61B 7/04; A61B 5/00;
(Continued)

(56) References Cited

U.S. PATENT DOCUMENTS 4,094,310 A    6/1978   McEachern et al.
4,632,122 A   12/1986   Johansson et al.
(Continued)

FOREIGN PATENT DOCUMENTS

DE    2644236 C3    4/1981
EP    0295497 B1    9/1993
(Continued)

OTHER PUBLICATIONS

PCT Search Report and Written Opinion for PCT Application No. PCT/US2016/023068, dated Jun. 3, 2016, 14 pages.
(Continued)

*Primary Examiner* — Carl H Layno
*Assistant Examiner* — Jon Eric C Morales
(74) *Attorney, Agent, or Firm* — Finch & Maloney PLLC

(57) ABSTRACT

In at least one example, a medical device is provided. The medical device includes at least one therapy electrode, at least one electrocardiogram (ECG) electrode, at least one acoustic sensor, and at least one processor coupled with the at least one acoustic sensor, the at least one ECG electrode, and the at least one therapy electrode. The at least one processor can receive at least one acoustic signal from the at least one acoustic sensor, receive at least one electrode signal from the ECG electrode, detect at least one unverified cardiopulmonary anomaly using the at least one electrode signal, and verify the at least one unverified cardiopulmonary anomaly with reference to data descriptive of the at least one acoustic signal.

25 Claims, 6 Drawing Sheets

(51) Int. Cl.
*A61B 5/00* (2006.01)
*A61B 5/0408* (2006.01)
*A61B 7/00* (2006.01)
*A61N 1/04* (2006.01)
*A61B 5/08* (2006.01)
*A61N 1/372* (2006.01)
*A61N 1/39* (2006.01)
*A61N 1/365* (2006.01)
*A61B 5/0464* (2006.01)

(52) U.S. Cl.
CPC ............... *A61B 7/003* (2013.01); *A61B 7/04* (2013.01); *A61N 1/046* (2013.01); *A61N 1/0484* (2013.01); *A61N 1/3655* (2013.01); *A61N 1/36542* (2013.01); *A61N 1/37247* (2013.01); *A61N 1/37258* (2013.01); *A61N 1/37282* (2013.01); *A61N 1/39* (2013.01); *A61N 1/3993* (2013.01); *A61B 5/0464* (2013.01); *A61B 5/4818* (2013.01); *A61B 5/6805* (2013.01); *A61B 5/6823* (2013.01); *A61B 5/6844* (2013.01); *A61B 5/721* (2013.01); *A61B 2562/0219* (2013.01); *A61B 2562/17* (2017.08)

(58) Field of Classification Search
CPC ... A61B 5/0205; A61B 5/0402; A61B 5/6833; A61B 5/04085; A61N 1/39; G10L 25/48
USPC ............ 600/587, 301, 509, 528, 586; 607/6; 704/270
See application file for complete search history.

(56) References Cited

U.S. PATENT DOCUMENTS

| | | |
|---|---|---|
| 4,928,690 A | 5/1990 | Heilman et al. |
| 4,978,926 A | 12/1990 | Zerod et al. |
| 4,991,217 A | 2/1991 | Garrett et al. |
| 5,062,834 A | 11/1991 | Gross et al. |
| 5,078,134 A | 1/1992 | Heilman et al. |
| 5,348,008 A | 9/1994 | Bornn et al. |
| 5,365,932 A | 11/1994 | Greenhut |
| 5,381,798 A | 1/1995 | Burrows |
| 5,472,453 A | 12/1995 | Alt |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,827,196 A | 10/1998 | Yeo et al. |
| 5,887,978 A | 3/1999 | Lunghofer et al. |
| 5,929,601 A | 7/1999 | Kaib et al. |
| 5,944,669 A | 8/1999 | Kaib et al. |
| 6,016,445 A | 1/2000 | Baura |
| 6,045,503 A | 4/2000 | Grabner et al. |
| 6,047,203 A | 4/2000 | Sackner et al. |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen et al. |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,304,783 B1 | 10/2001 | Lyster et al. |
| 6,390,996 B1 | 5/2002 | Halperin et al. |
| 6,406,426 B1 | 6/2002 | Reuss et al. |
| 6,681,003 B2 | 1/2004 | Linder et al. |
| 6,690,969 B2 | 2/2004 | Bystrom et al. |
| 6,804,554 B2 | 10/2004 | Ujhelyi et al. |
| 6,827,695 B2 | 12/2004 | Palazzolo et al. |
| 6,878,121 B2 | 4/2005 | Krausman et al. |
| 6,908,437 B2 | 6/2005 | Bardy |
| 6,947,565 B2 | 9/2005 | Halleck et al. |
| 6,961,612 B2 | 11/2005 | Elghazzawi et al. |
| 6,990,373 B2 | 1/2006 | Jayne et al. |
| 7,149,579 B1 | 12/2006 | Koh et al. |
| 7,220,235 B2 | 5/2007 | Geheb et al. |
| 7,340,296 B2 | 3/2008 | Stahmann et al. |
| 7,453,354 B2 | 11/2008 | Reiter et al. |
| 7,488,293 B2 | 2/2009 | Marcovecchio et al. |
| 7,712,373 B2 | 5/2010 | Nagle et al. |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,412,323 B2 | 4/2013 | Bauer |
| 2003/0004547 A1 | 1/2003 | Owen et al. |
| 2003/0060723 A1 | 3/2003 | Joo et al. |
| 2003/0095648 A1 | 5/2003 | Kaib et al. |
| 2003/0109904 A1 | 6/2003 | Silver et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2004/0049233 A1 | 3/2004 | Edwards |
| 2004/0162510 A1 | 8/2004 | Jayne et al. |
| 2004/0249419 A1 | 12/2004 | Chapman et al. |
| 2005/0049515 A1 | 3/2005 | Misczynski et al. |
| 2005/0131465 A1 | 6/2005 | Freeman et al. |
| 2005/0246199 A1 | 11/2005 | Futch |
| 2005/0283198 A1 | 12/2005 | Haubrich et al. |
| 2006/0036292 A1 | 2/2006 | Smith et al. |
| 2006/0085049 A1 | 4/2006 | Cory et al. |
| 2006/0178706 A1 | 8/2006 | Lisogurski et al. |
| 2006/0211934 A1 | 9/2006 | Hassonjee et al. |
| 2006/0270952 A1 | 11/2006 | Freeman et al. |
| 2006/0293714 A1 | 12/2006 | Salo et al. |
| 2007/0118056 A1 | 5/2007 | Wang et al. |
| 2007/0143864 A1 | 6/2007 | Cabana et al. |
| 2007/0161913 A1 | 7/2007 | Farrell et al. |
| 2007/0169364 A1 | 7/2007 | Townsend et al. |
| 2007/0197878 A1 | 8/2007 | Shklarski |
| 2007/0239214 A1 | 10/2007 | Cinbis |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0021532 A1 | 1/2008 | Kveen et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0103402 A1 | 5/2008 | Stickney et al. |
| 2008/0167535 A1 | 7/2008 | Stivoric et al. |
| 2008/0177341 A1 | 7/2008 | Bowers |
| 2008/0249591 A1 | 10/2008 | Gaw et al. |
| 2008/0287749 A1 | 11/2008 | Reuter |
| 2008/0294019 A1 | 11/2008 | Tran |
| 2008/0306560 A1 | 12/2008 | Macho et al. |
| 2008/0312520 A1 | 12/2008 | Rowlandson et al. |
| 2008/0312522 A1 | 12/2008 | Rowlandson et al. |
| 2008/0312709 A1 | 12/2008 | Vople et al. |
| 2009/0018428 A1 | 1/2009 | Dias et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |

(56) References Cited

U.S. PATENT DOCUMENTS

| | | |
|---|---|---|
| 2009/0076559 A1 | 3/2009 | Libbus et al. |
| 2009/0093687 A1 | 4/2009 | Telfort et al. |
| 2009/0138059 A1 | 5/2009 | Ouwerkerk |
| 2009/0146822 A1 | 6/2009 | Soliman |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0281394 A1 | 11/2009 | Russell et al. |
| 2009/0287120 A1 | 11/2009 | Ferren et al. |
| 2009/0292194 A1 | 11/2009 | Libbus et al. |
| 2009/0295326 A1 | 12/2009 | Daynes et al. |
| 2009/0307266 A1 | 12/2009 | Fleizach et al. |
| 2009/0318779 A1 | 12/2009 | Tran |
| 2010/0052892 A1 | 3/2010 | Allen et al. |
| 2010/0052897 A1 | 3/2010 | Allen et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0081962 A1 | 4/2010 | Hamaguchi et al. |
| 2010/0114243 A1 | 5/2010 | Nowak et al. |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0298899 A1 | 11/2010 | Donnelly et al. |
| 2011/0015533 A1 | 1/2011 | Cox et al. |
| 2011/0093840 A1 | 4/2011 | Pynenburg et al. |
| 2011/0098765 A1 | 4/2011 | Patel |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0053479 A1 | 3/2012 | Hopenfeld |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2013/0060149 A1 | 3/2013 | Song et al. |
| 2013/0325078 A1 | 12/2013 | Whiting et al. |
| 2014/0277243 A1 | 9/2014 | Maskara et al. |
| 2015/0005588 A1 | 1/2015 | Herken et al. |

FOREIGN PATENT DOCUMENTS

| | | |
|---|---|---|
| EP | 0335356 B1 | 3/1996 |
| EP | 1455640 B1 | 1/2008 |
| EP | 1720446 B1 | 7/2010 |
| JP | 5115450 A | 5/1993 |
| JP | 2002200059 A | 7/2002 |
| WO | 200002484 A1 | 1/2000 |
| WO | 2004054656 A1 | 7/2004 |
| WO | 2004067083 A2 | 8/2004 |
| WO | 2004078259 A1 | 9/2004 |
| WO | 2005082454 A1 | 9/2005 |
| WO | 2006050325 A2 | 5/2006 |
| WO | 2007019325 A2 | 2/2007 |
| WO | 2009034506 A1 | 3/2009 |
| WO | 2010025432 A1 | 3/2010 |
| WO | 2010077997 A2 | 7/2010 |

OTHER PUBLICATIONS

De Bock et al., "Captopril Treatment of Chronic Heart Failure in the Very Old", Journal of Gerontology: Medical Sciences, 1994, pp. M148-M152, vol. 49, No. 3.

http://web.archive.org/web/20030427001846/http:/www.lifecor.com/imagelib/imageproduct.asp; Published by LifeCor, Inc., 2002, on webpage owned by LifeCor, Inc.

"ATS Statement: Guidelines for the Six-Minute Walk Test", American Journal of Respiratory and Critical Care Medicine, 2002, pp. 111-117, vol. 166, American Thoracic Society, , available at http://ajrccm.atsjournals.org/cgi/content/full/166/1/111.

O'Keeffe et al., "Reproductivity and Responsiveness of Quality of Life Assessment and Six Minute Walk Test in Elderly Heart Failure Patients", Heart, 1998, 80: 377-382.

MEDICAL DEVICE WITH ACOUSTIC SENSOR

RELATED APPLICATIONS

This application claims benefit under 35 U.S.C. § 119(e) of U.S. Provisional Application Ser. No. 62/134,881, titled "MEDICAL DEVICE WITH ACOUSTIC SENSOR," filed Mar. 18, 2015, which is hereby incorporated herein by reference in its entirety.

BACKGROUND

Technical Field

This disclosure relates to medical devices, and more particularly to medical devices that monitor the cardiopulmonary system using one or more acoustic sensors.

Discussion

Some conventional medical devices that monitor the cardiopulmonary system obtain a subject's electrocardiogram (ECG) signal from body surface electrodes. Determining the true characteristics of an ambulatory subject's cardiac cycle based on an ECG signal in this manner can be difficult. Electrical noise and electrode fall-off frequently degrade the quality of the ECG signal. In addition, the characteristics of ECG signals vary from subject to subject due to factors such as the subject's state of health and individual physiology.

Known ambulatory wearable defibrillators, such as the LifeVest® Wearable Cardioverter Defibrillator available from ZOLL Medical Corporation of Chelmsford, Mass., use four ECG sensing electrodes in a dual-channel configuration. That is, an electrical signal provided by one of the four ECG sensing electrodes is paired with the electrical signal provided by another of the four ECG sensing electrodes to form a channel. This arrangement of ECG sensing electrodes is usually suitable because in most cases it is rare that noise or electrode movement affects the entire body circumference. The dual-channel configuration provides redundancy and allows the system to operate on a single channel if necessary. Because signal quality also varies from subject to subject, having two channels provides the opportunity to have improved signal pickup, since the ECG sensing electrodes are located in different body positions.

SUMMARY

Some aspects and examples disclosed herein manifest an appreciation for the sporadic inability of medical devices relying solely on conventional ECG sensing electrodes to determine the functional effect of a cardiopulmonary anomaly. For example, medical devices in accord with at least one example disclosed herein utilize a combination of electrode and acoustic sensor data to detect cardiopulmonary anomalies with increased accuracy and precision relative to conventional ECG sensing electrode based systems. With this enhanced cardiopulmonary data, various medical devices disclosed herein are better able to discriminate between detected cardiopulmonary anomalies that substantially impair cardiac or pulmonary function and those that do not. Using the enhanced cardiopulmonary data, these medical devices may modify the manner in which treatment is provided to a subject. For example, the medical devices may treat those anomalies that substantially impair cardiopulmonary function and may defer treatment where cardiopulmonary function is not substantially impaired.

In at least one example, a medical device is provided. The medical device includes at least one therapy electrode, at least one electrocardiogram (ECG) electrode, at least one acoustic sensor, and at least one processor coupled with the at least one acoustic sensor, the at least one ECG electrode, and the at least one therapy electrode. The at least one processor can receive at least one acoustic signal from the at least one acoustic sensor, receive at least one electrode signal from the ECG electrode, detect at least one unverified cardiopulmonary anomaly using the at least one electrode signal, and verify the at least one unverified cardiopulmonary anomaly with reference to data descriptive of the at least one acoustic signal.

In the medical device, the data descriptive of the acoustic signal includes at least one of S1, S2, S3, S4, EMAT, % EMAT, SDI, and LVST. The unverified cardiopulmonary anomaly includes at least one of supraventricular tachycardia, ventricular tachycardia, pulseless electrical activity, asystole, a heart murmur, sleep apnea, and respiratory failure. The at least one processor can verify disconnection of the at least one ECG electrode with reference to the data descriptive of the at least one acoustic signal.

The medical device may further include at least one accelerometer coupled with the at least one processor, wherein the at least one processor can further verify the at least one unverified cardiopulmonary anomaly with reference to data descriptive of at least on motion signal from the at least one accelerometer. In the medical device, the at least one processor can acquire and record the at least one acoustic signal during a configurable period of time. The at least one processor can also execute a sleep test in response to receiving input requesting the sleep test.

In another example, a medical device is provided. The medical device includes at least one electrocardiogram (ECG) electrode, at least one acoustic sensor, and at least one processor coupled with the at least one acoustic sensor and the at least one ECG electrode and configured to receive at least one acoustic signal from the at least one acoustic sensor, to receive at least one electrical signal from the at least one ECG electrode, and to detect at least one cardiopulmonary anomaly using the at least one electrical signal and the at least one acoustic signal. The medical device may include an ambulatory medical device.

In the medical device, the at least one processor may be configured to detect the at least one cardiopulmonary anomaly at least in part by identifying the at least one cardiopulmonary anomaly using the at least one electrical signal and verifying the at least one cardiopulmonary anomaly using the at least one acoustic signal. The medical device may further include a garment. The at least one ECG electrode and the at least one acoustic sensor may be integrated with the garment. The medical device may further include at least one therapy electrode coupled with the at least one processor and integrated with the garment. The at least one acoustic signal may include at least one of S1, S2, S3, and S4. The at least one processor may be configured to detect the at least one cardiopulmonary anomaly at least in part by calculating, based on the at least one acoustic signal, at least one of electromechanical activation time (EMAT), EMAT as a percentage of cardiac cycle time, systolic dysfunction index, and left ventricular systolic time. The at least one cardiopulmonary anomaly may include at least one of supraventricular tachycardia, ventricular tachycardia, pulseless electrical activity, asystole, a heart murmur, sleep apnea, and respiratory failure.

In the medical device, the at least one processor may be configured to detect disconnection of the at least one ECG electrode based on the at least one acoustic signal. The medical device may further include at least one motion sensor coupled with the at least one processor. The at least processor may be configured to receive at least one motion signal from the at least one motion sensor and to detect the at least one cardiopulmonary anomaly using the at least one electrical signal, the at least one acoustic signal, and the at least one motion signal.

In the medical device, the at least one acoustic sensor may include at least one motion sensor. The at least one acoustic sensor may include at least one accelerometer. The at least processor may be configured to receive at least one signal from the at least one accelerometer and to partition the at least one signal into the at least one acoustic signal and at least one motion signal. The at least one motion signal may include frequencies less than approximately 10 hertz. The at least one acoustic signal may include frequencies greater than approximately 10 hertz. The at least one processor may be configured to partition the at least one signal into a first frequency band for subject motion, a second frequency band for chest compression motion and/or sounds, a third frequency band for heart sounds, and a fourth frequency band for breath sounds. The first frequency band may include frequencies less than approximately 6 hertz, the second frequency band may include frequencies between approximately 6 and 20 hertz, the third frequency band may include frequencies between approximately 20 hertz and 150 hertz, and the fourth frequency band may include frequencies between approximately 300 to 1200 hertz.

In another example, a method of monitoring a subject using a wearable defibrillator is provided. The wearable defibrillator includes at least one electrocardiogram (ECG) electrode and at least one acoustic sensor. The method comprises acts of receiving at least one acoustic signal from the at least one acoustic sensor, receiving at least one electrical signal from the at least one ECG electrode, and detecting at least one cardiopulmonary anomaly using the at least one electrical signal and the at least one acoustic signal.

In the method, the act of receiving the at least one acoustic signal may include an act of receiving at least one of S1, S2, S3, and S4. The act of detecting the at least one cardiopulmonary anomaly may include an act of calculating, based on the at least one acoustic signal, at least one of electromechanical activation time (EMAT), EMAT as a percentage of cardiac cycle time, systolic dysfunction index, and left ventricular systolic time. The act of detecting the at least one cardiopulmonary anomaly may include an act of detecting at least one of supraventricular tachycardia, ventricular tachycardia, pulseless electrical activity, asystole, a heart murmur, sleep apnea, and respiratory failure.

The medical device may further include at least one motion sensor. The method may further include acts of receiving at least one motion signal from the at least one motion sensor and detecting the at least one cardiopulmonary anomaly using the at least one electrical signal, the at least one acoustic signal, and the at least one motion signal.

In another example, a medical device is provided. The medical device includes a memory, at least one accelerometer, and at least one processor coupled with the at least one accelerometer and the memory. The at least one processor is configured to receive at least one acoustic signal from the at least one accelerometer, to receive at least one motion signal from the at least one accelerometer, and to execute a sleep test configured to store data descriptive of the at least one acoustic signal and the at least one motion signal in the memory.

The medical device may further include comprising at least one ECG electrode coupled with the at least one processor. The at least one processor may be configured to receive at least one electrical signal from the at least one ECG electrode and the sleep test is configured to store data descriptive of the at least one electrical signal in the memory. The medical device may further include a garment. The at least one ECG electrode and the at least one accelerometer may be integrated with the garment. The medical device may further include at least one therapy electrode coupled with the at least one processor and integrated with the garment. The at least one processor may be configured to execute the sleep test at a configurable time. The medical device may further include at least one motion sensor distinct from the accelerometer and coupled with the at least one processor. The at least one motion sensor may be positioned on a wrist of a subject. The at least one processor may be configured to receive one or more motion signals from the at least one motion sensor. The sleep test may be configured to store data descriptive of the one or more motion signals in the memory.

Still other aspects and advantages of the examples disclosed herein are discussed in detail below. Moreover, it is to be understood that both the foregoing information and the following detailed description are merely illustrative examples of various aspects, and are intended to provide an overview or framework for understanding the nature and character of the claimed subject matter. Any example disclosed herein may be combined with any other example. References to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings.

DETAILED DESCRIPTION

Figure 1:
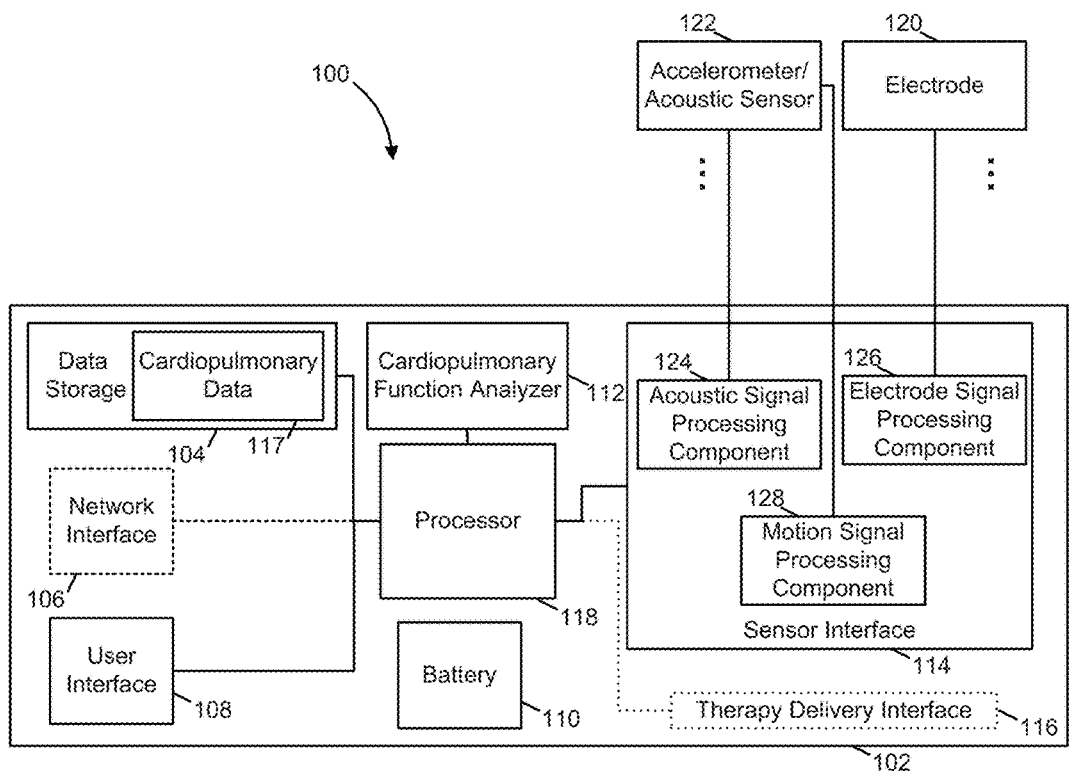
FIG. 1 is a functional schematic one example of a pacing device.

Medical devices in accord with various examples disclosed herein utilize enhanced cardiopulmonary data to implement a wide variety of functionality. For instance, according to some examples, a medical device includes a cardiopulmonary function analyzer configured to process enhanced cardiopulmonary data, which may include acoustic and electrode signals among other signals, to identify cardiopulmonary anomalies that are difficult to detect using conventional ECG sensing electrodes. Examples of these cardiopulmonary anomalies include super ventricular tachycardia (SVT) as distinct from ventricular tachycardia (VT), asystole, ECG sensing electrode falloff, pulseless electrical activity (PEA), asystole, pseudo-PEA, bradycardia, heart murmurs, sleep apnea, and respiratory arrest.

In some examples, the cardiopulmonary function analyzer also determines how to address the identified cardiopulmonary anomaly. For example, where the medical device is a monitor, the cardiopulmonary function analyzer may issue an alarm describing the anomaly to an external entity, such as a user or a computer system distinct from the medical device. Where the medical device is a defibrillator, the cardiopulmonary function analyzer may address the anomaly by delivering a defibrillating shock to a subject. Where the medical device is a pacing device, the cardiopulmonary function analyzer may address the anomaly by delivering one or more pacing pulses.

Any of the medical devices disclosed herein may be non-invasive, bodily-attached, or ambulatory. As used herein, the term non-invasive means that the device does not penetrate the body of a subject. This is in contrast to invasive devices, such as implantable medical devices, in which at least a portion of the device is disposed subcutaneously. The term bodily-attached means that at least a portion of the device (other than its electrodes in the case of a defibrillator, cardioverter, or pacer) is removably attached to the body of a subject, such as by mechanical coupling (e.g., by a wrist strap, cervical collar, bicep ring), adhesion (e.g., by an adhesive gel intermediary), suction, magnetism, fabric or other flexible material (e.g., by straps or integration into a garment) or other body mounting features not limited by the aforementioned examples. These coupling elements hold the device in a substantially fixed position with respect to the body of the subject. The term ambulatory means that the device is capable of and designed for moving with the subject as the subject goes about their daily routine.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Medical Device

Various examples disclosed herein utilize enhanced cardiopulmonary data (e.g., acoustic data and electrode data) to detect and treat cardiopulmonary anomalies, such as SVT as distinct from VT, asystole, ECG sensing electrode falloff, PEA, pseudo-PEA, bradycardia, heart murmurs, sleep apnea, and respiratory arrest. FIG. 1 illustrates a medical device 100 in accord with some examples. As shown in FIG. 1, the medical device 100 includes a medical device controller 102, one or more accelerometers/acoustic sensors 122, and one or more electrodes 120. As illustrated in FIG. 1, the medical device controller 102 includes a processor 118, a sensor interface 114, a cardiopulmonary function analyzer 112, a therapy delivery interface 116, data storage 104, a network interface 106, a user interface 108, and a battery 110. The processor 118 can be implemented using a variety of commercially available processors. Specific examples of the processor 118 are described further below. The data storage 104 includes cardiopulmonary data 117. The sensor interface 114 can include an acoustic signal processing component 124, an electrode signal processing component 126, and motion signal processing component 128. In some implementations, components such as cardiopulmonary function analyzer 112 and sensor interface 114 can be implemented within processor 118. In some implementations, the components can be implemented in circuitry that is separate from processor 118.

The medical device 100 may be any of a variety of medical devices including defibrillators, monitors, CPR systems, pacing devices, and other medical devices. More specific examples of medical devices in accord with the medical device 100 are described further below with reference to FIGS. 2-4.

As shown in FIG. 1, the acoustic signal processing component 124 is coupled to and receives acoustic signals from the accelerometer/acoustic sensor 122. Similarly, the electrode signal processing component 126 is coupled to and receives electrode signals from the electrode 120. The electrode 120 may comprise any of a variety of commercially available electrodes, some examples of which are described further below.

Likewise, the motion signal processing component 128 is coupled to and receives motion signals from the accelerometer/acoustic sensor 122. As illustrated in FIG. 1, in some examples, the cardiopulmonary function analyzer 112 can be coupled with (via the processor 118) and receive processed acoustic data from the acoustic signal processing component 124, processed electrode data from the electrode signal processing component 126, and processed motion data from the motion signal processing component 128. Examples of processes executed by the acoustic signal processing component 124, the electrode signal processing component 126, and the motion signal processing component 128 are described further below with reference to FIG. 5.

According to one example illustrated by FIG. 1, the cardiopulmonary function analyzer 112 is configured to detect heart beats, breath sounds, and cardiopulmonary anomalies and determine whether the detected anomalies substantially impair cardiac or pulmonary function. For example, the cardiopulmonary function analyzer 112 can be implemented using a variety of hardware or software components. When executing according to this configuration, in some examples, the cardiopulmonary function analyzer 112 detects cardiopulmonary anomalies by scanning processed acoustic data and processed electrode data for patterns indicative of cardiopulmonary anomalies. Responsive to identifying a data pattern indicative of a cardiopulmonary anomaly, the cardiopulmonary function analyzer 112 identifies a routine to address the cardiopulmonary anomaly based on the identity of the anomaly and a confidence that the anomaly actually exists. Next, the cardiopulmonary function analyzer 112 initiates the identified routine. The data patterns scanned for by the cardiopulmonary function analyzer 112 are indicative of a wide variety of cardiopulmonary anomalies. Examples of these anomalies include cardiac arrhythmias (e.g., bradycardia, tachycardia, SVT, an irregular cardiac rhythm, PEA, and asystole), murmurs, sleep apnea, and respiratory arrest. The data patterns may also indicate problems with the medical device itself such as faulty or disconnected sensors. Specific examples of the data patterns scanned for by the cardiopulmonary function analyzer 112 and actions taken responsive to detection of the data patterns are described further below with reference to FIG. 5.

In some examples, the cardiopulmonary function analyzer 112 is configured to leverage the differing originating modalities of the processed acoustic data and electrode data to advantageous effect. For example, data patterns that indicate VT are sometimes present in processed electrode data where the subject is actually experiencing SVT. Accordingly, in an implementation, the cardiopulmonary function analyzer 112 can analyze the processed acoustic data to determine whether VT indicated by the processed electrode data actually exists. If the cardiopulmonary function analyzer 112 determines based on the processed acoustic data that no VT condition exists, the cardiopulmonary function analyzer 112 may not initiate treatment as doing so may convert SVT into VT, which poses a greater risk to the health of the subject than SVT. In some examples, as described further below with reference to FIG. 5, the cardiopulmonary function analyzer 112 verifies that no VT condition exists by comparing the intensity and variability of S1 to predefined thresholds. S1 is a heart sound described further below.

Similarly, in some examples, the cardiopulmonary function analyzer 112 can analyze processed acoustic data to determine whether the heart of a subject is mechanically pumping blood where the processed electrode data indicates asystole or PEA. If sufficient blood is being pumped (e.g., if the ejection fraction exceeds a predefined threshold), the cardiopulmonary function analyzer 112 may defer treatment. In some examples, as described further below with reference to FIG. 5, the cardiopulmonary function analyzer 112 determines whether the ejection fraction exceeds the predefined threshold by comparing EMAT to a predefined threshold. EMAT is a metric calculated based on heart sounds and is described further below.

In some examples, the cardiopulmonary function analyzer 112 can analyze processed acoustic data that covers periods of time where electrode data is not available (e.g., due to an enforced blanking interval, temporary electrode saturation, or electrode fall off) and takes appropriate action based on the condition of a subject as indicated by the processed acoustic data.

In some implementations, the cardiopulmonary function analyzer 112 can analyze processed acoustic data and processed motion data received via multiple signals generated by the accelerometer/acoustic sensor 122. In this regard, the sensor 122 can provide the signals over one or more channels to maintain signal separation. In some implementations, the multiple signals can be combined or multiplexed within a signal channel. For example, the cardiopulmonary function analyzer 112 may analyze data representative of a subject's respiration encoded from a first channel, data representative of a subject's heart sounds encoded from a second channel, and data representative of a subject's position encoded from a third channel.

Figure 5:
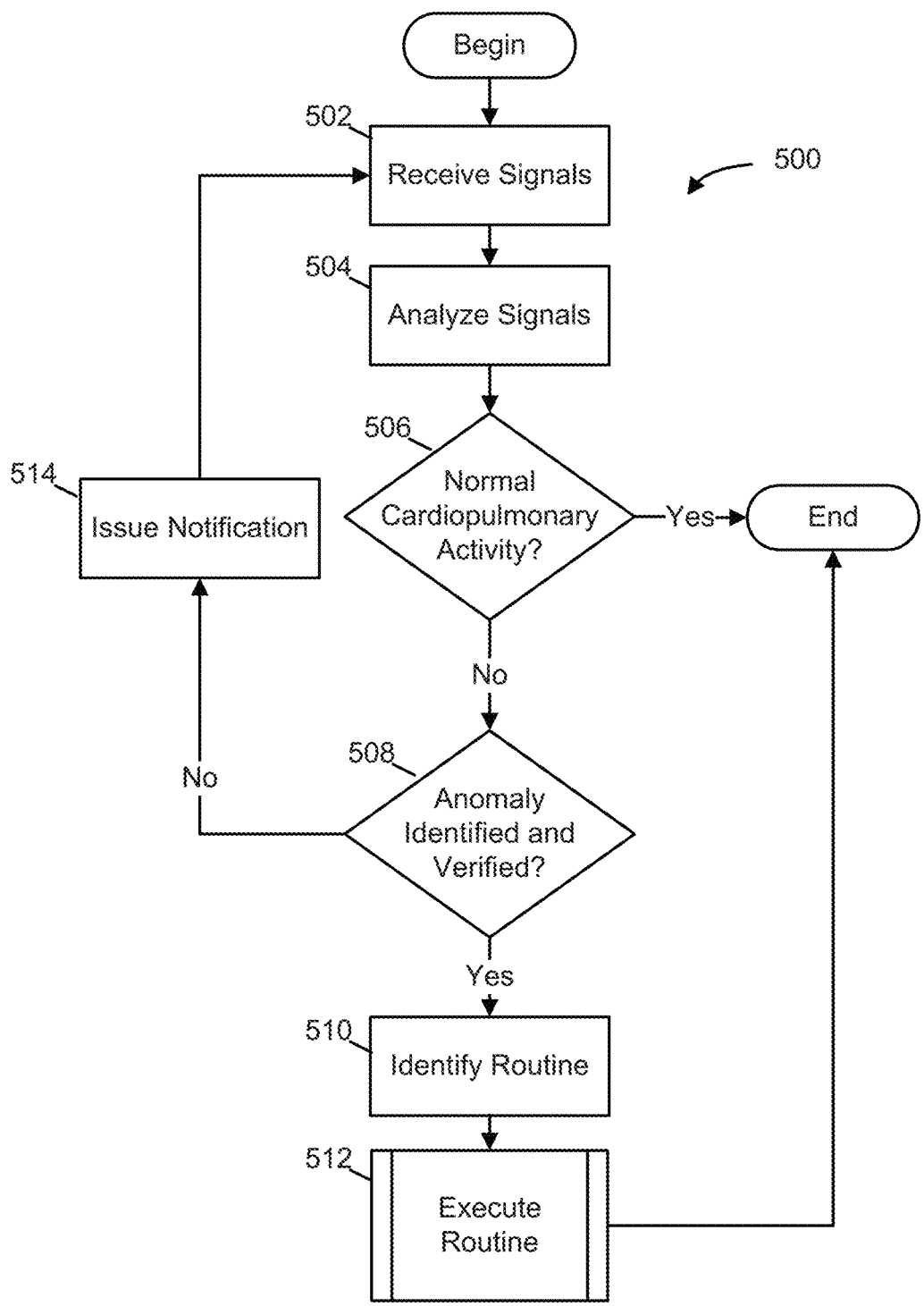
FIG. 5 is a flow diagram of one example of a process analyzing enhanced cardiopulmonary data.

One example of a cardiopulmonary anomaly detection process that the cardiopulmonary function analyzer 112 is configured to execute is described further below with reference to FIG. 5.

In some implementations, the cardiopulmonary function analyzer 112 can be configured to execute an at-home sleep test. When executing according to this configuration, the cardiopulmonary function analyzer 112 may receive information indicating that a user has requested execution of the sleep test via a user interface of the medical device, such as the user interface 108. Responsive to receipt of this request information, the cardiopulmonary function analyzer 112 can record and store enhanced cardiopulmonary data for a configurable period of time (e.g., 6-10 hours) specified in the request information or within a discrete configurable parameter of the medical device. This period of time may, for example, represent time when the subject is expected to be asleep. Enhanced cardiopulmonary data can include information based on one or more of the processed signals from the sensor interface 114 and can include motion data, acoustic data, electrode data, or aggregated data generated by processing other data. In some examples, the configurable period of time can include a future time period (e.g., 2 days from the current day) or a reoccurring period (e.g., every other Tuesday for the next month). Upon completion of each sleep test recording, the cardiopulmonary function analyzer 112 may transmit the recorded data to a remote system via, for example, a network interface, such as the network interface 106.

In some examples, the medical device 100 can generate a variety of reports and metrics based on the data analyzed by the cardiopulmonary function analyzer 112. For example, the medical device 100 can cause a report to be presented to a user via the user interface 108. In some cases, the medical device 100 can cause a report (and any associated analytic metrics) to be transmitted to a network output device (e.g., a network printer on a same or different network as the medical device 100). In some instances, the report can be transmitted to a server on same or different network (e.g. at a remote location) for further processing and storage.

In an example, the cardiopulmonary function analyzer 112 may generate both summary and full disclosure reports in portable document format for each recorded period. The cardiopulmonary function analyzer 112 may save or print these reports in response to a request for the same. The full disclosure report that depicts all enhanced cardiopulmonary data (e.g., electrode data and acoustic data) for each recorded period. The summary report summaries the information presented in the full disclosure report.

In some examples, the variety of reports include one or more reports that present information descriptive of the hemodynamic performance of the heart and respiratory effort of a subject. For instance, a report may provide information descriptive of chest rise and fall during respiration as determined from acoustic vibration of the chest wall during respiration. These reports may also display information descriptive of the restlessness of a subject, as determined from processed motion data. This processed motion data may be generated by one or more accelerometers positioned on the torso and wrist of a subject, such as within a pocket, belt, or watch worn by the subject and in communication with the cardiopulmonary function analyzer 112 via a BAN. For example, such data may provide insights into a subject's body position during sleep or limb movements and position. The processed motion data may also be generated by an internal 3-axis gyroscope included in some examples.

In some examples, the cardiopulmonary function analyzer 112 reads values of one or more configurable parameters that specify targeted operational characteristics of the cardiopulmonary function analyzer 112. These operational parameters may include upload filter criteria that specifies the data type and frequency with which the cardiopulmonary function analyzer 112 transmits enhanced cardiopulmonary data to a remote computer, such as the centralized server described further below with reference to FIG. 2 via the network interface 106.

In some examples illustrated by FIG. 1, the acoustic signal processing component 124 is configured to detect and record a variety of sounds related to cardiopulmonary function. To process analog and digital acoustic signals received from the accelerometer/acoustic sensor 122, the acoustic signal processing component 124 may include various circuitry, such as amplifiers, filters, transducers, analog to digital converters, analog signal processors, and digital signal processors. In at least one example, the acoustic signal processing component 124 processes signals received from one or more acoustic channels. Further according to some examples, the acoustic signal processing component 124 transmits processed acoustic data descriptive of the acoustic signals to the cardiopulmonary function analyzer 112 for subsequent analysis. In some examples, the processor 118 exchanges data with the sensor interface 114 and executes the cardiopulmonary function analyzer 112. Additional aspects and functions of the processor 118 are described further below.

In healthy adults, there are at least two normal heart sounds, commonly referred to as S1 and S2. A third heart sound, commonly referred to as S3 (also called a protodiastolic gallop or ventricular gallop), may be indicative of a problem with a subject's heart when present. For example, in subjects over 40 years old, S3 has been associated with an abnormal diastolic filling pattern. The presence of S3 may signal cardiac problems like a failing left ventricle as in dilated congestive heart failure. A fourth heart sound, commonly referred to as S4 (also called a presystolic gallop or atrial gallop), is indicative of a problem with a subject's heart when present. For example, S4 is often associated with an increased left ventricular stiffness. Heart murmurs may also be present in some subjects and may indicate cardiac problems.

In some examples, the acoustic signal processing component 124 is configured to detect and record heart sound values including any one or all of S1, S2, S3, and S4. Other heart sound values which may be monitored and recorded by the acoustic signal processing component 124 may include any one or more of electromechanical activation time (EMAT), percentage of EMAT (% EMAT), systolic dysfunction index (SDI), and left ventricular systolic time (LVST).

EMAT is generally measured from the onset of the Qwave on the ECG to the closure of the mitral valve within the S1 heart sound. Prolonged EMAT has been associated with reduced left ventricular ejection fraction (LV EF, being a measure of how much blood is being pumped out of the left ventricle of the heart with each contraction).

% EMAT is EMAT divided by a dominant RR interval. In this regard, % EMAT is related to an efficiency of the pump function of the heart.

SDI is a multiplicative combination of ECG and heart sound values (EMA, S3, QRS duration and QR interval). SDI can be used to predict left ventricular systolic dysfunction.

LVST is the systolic portion of the cardiac cycle and is defined as the time interval between the S1 and the S2 heart sounds. LVST may have some heart rate dependence, and can be approximately 40% (range 30-50%) of the cardiac cycle. LVST can be affected by disease that produces poor contractility or a low ejection fraction.

In some examples, during an initial fitting of the medical device, the medical device may record enhanced cardiopulmonary data to use as a baseline for an individual subject. For example, a baseline EMAT may be recorded and later used to analyze degree of degradation occurring within the cardiopulmonary function of the subject. In one example, the baseline EMAT and baseline ejection fraction can be recorded and subsequent EMAT values can be used to approximate subsequent ejection fractions.

In some examples, the recorded heart sound values described above may be stored in non-volatile data storage. For example, in one example these values are stored as cardiopulmonary data 117 within the data storage 104. In at least one example, the cardiopulmonary function analyzer 112 periodically monitors the recorded heart sound values for events of interest. In this example, where the recorded heart sound values indicate a potential health risk, the cardiopulmonary function analyzer 112 may notify an external entity of the risk. For example, where an EMAT value degrades gradually over a specified period of time, the cardiopulmonary function analyzer 112 may transmit a communication to a healthcare provider indicating this degradation.

In other examples, when executing according to its configuration, the acoustic signal processing component 108 identifies and records breathing sounds such as those that accompany normal respiration, snoring, episodes of sleep apnea, and respiratory arrest.

In some examples, the acoustic signal processing component 124 reads values of one or more configurable parameters that specify targeted operational characteristics of the acoustic signal processing component 124 or the accelerometer/acoustic sensor 122. These operational parameters may specify the sampling rate, filter coefficients, recording duration and interval, and noise thresholds, used to process acoustic data. The value of the recording duration and interval operational parameter specifies the length of time of each acoustic recording and the interval of time between recordings. In one example, the value of the recording duration and interval operational parameter specifies a duration of 5 seconds to be recorded every 10 minutes. In some examples, the acoustic signal processing component 124 and the accelerometer/acoustic sensor 122 continuously record, process, and store processed acoustic data.

In one example illustrated by FIG. 1, the electrode signal processing component 126 is configured to detect and record cardiac activity of a subject. For example, when executing according to this configuration, the electrode signal processing component 126 may detect and record ECG signals. Further according to this example, the electrode signal processing component 126 transmits information descriptive of the ECG signals to the cardiopulmonary function analyzer 112 for subsequent analysis. As described above, the processed data from the electrode signal processing component 126 can be monitored for cardiopulmonary anomalies either alone or in combination with processed data from the acoustic signal processing component 124 or the motion signal processing component 128.

In one example illustrated by FIG. 1, the motion signal processing component 128 is configured to detect and record motion and physical movement of a subject. For example, when executing according to this configuration, the motion signal processing component 128 may detect and record physical movement such as walking, falling, breath motion (e.g., chest rising and falling), and the like. Further according to this example, the motion signal processing component 128 transmits information descriptive of the accelerometer signals to the cardiopulmonary function analyzer 112 for subsequent analysis.

In one example illustrated by FIG. 1, the accelerometer/acoustic sensor 122 may comprise any device that may detect sounds from a subject's cardiopulmonary system and provide an output signal responsive to the detected heart and breath sounds. In some examples the accelerometer/acoustic sensor 122 comprises a microphone or an accelerometer. In some examples, the accelerometer comprises a microelectromechanical system (MEMS) accelerometer or a multi-channel accelerometer, for example, a three channel accelerometer. The acoustic sensor may comprise a three channel accelerometer configured to sense movement in each of three orthogonal axes. An example accelerometer which may be utilized in some examples is a LIS344ALH accelerometer, available from STMicroelectronics.

The accelerometer/acoustic sensor 122 and associated electronics may be configured to monitor any one or more of a subject's respiration, a subject's heart sounds, a subject's position, and an activity level of a subject. The accelerometer/acoustic sensor 122 and associated electronics may additionally or alternatively be configured to monitor other sounds which may be indicative of a state of health of a subject, for example, gastrointestinal sounds or the sounds of snoring or the absence of such sounds to, for example, provide an indication of the subject experiencing sleep apnea or respiratory arrest. The accelerometer/acoustic sensor 122 may provide signals indicative of the subject's heart sounds on a first channel, signals indicative of the subject's position on a second channel, and signals indicative of the subject's activity level on a third channel. In some examples, the different channels may be utilized to provide signals indicative of more than one physiological characteristic or other characteristics associated with the state of the subject. For example, the accelerometer/acoustic sensor 122 may provide signals indicative of the subject's heart sounds on a first channel, signals indicative of the subject's respiration on a second channel, and signals indicative of the subject's body position on any or all of the first, second, and a third channel. It should be appreciated that dependent on the underlying characteristic that is being monitored, multiple signals related to the characteristic being monitored may be received over a single channel or a number of different channels.

Figure 4:
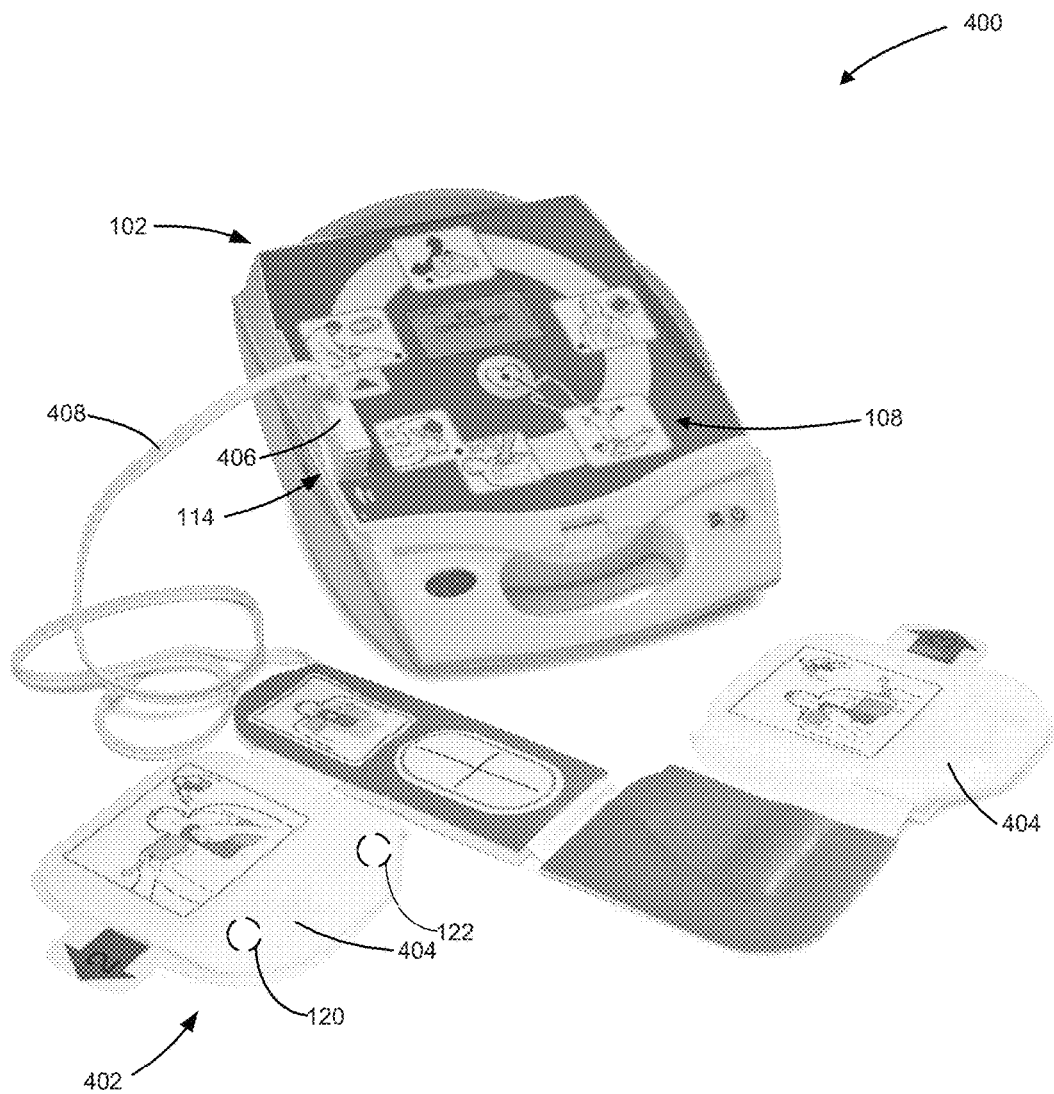
FIG. 4 is an illustration of one example of an external medical device.

In one example illustrated by FIG. 1, the electrode 120 may include any type of sensing electrode, such as one or more ECG sensing electrodes as described further below with reference to FIGS. 2 and 4.

In some examples in accord with FIG. 1, the battery 110 is a rechargeable 3 cell 2200 mAh lithium ion battery pack that provides electrical power to the other device components with a minimum 24 hour runtime between charges. It is appreciated that the battery capacity, runtime, and type (e.g., lithium ion, nickel-cadmium, or nickel-metal hydride) may be changed to best fit the specific application of the medical device controller 102.

According to the example illustrated in FIG. 1, the processor 118 is coupled to the sensor interface 114, the therapy delivery interface 116, the data storage 104, the network interface 106, and the user interface 108. The processor 118 performs a series of instructions that result in manipulated data which are stored in and retrieved from the data storage 104. According to a variety of examples, the processor 118 is a commercially available processor such as a processor manufactured by Texas Instruments, Intel, AMD, Sun, IBM, Motorola, Freescale, and ARM Holdings. However, the processor 118 may be any type of processor, multiprocessor or controller, whether commercially available or specially manufactured. For instance, according to one example, the processor 118 may include a power conserving processor arrangement as described in U.S. Pat. No. 8,904,214, titled SYSTEM AND METHOD FOR CONSERVING POWER IN A MEDICAL DEVICE, issued Dec. 2, 2014, which is hereby incorporated herein by reference in its entirety. In one example, the processor 118 is an Intel® PXA270.

In addition, in several examples the processor 118 is configured to execute a conventional real-time operating system (RTOS), such as RTLinux. In these examples, the RTOS may provide platform services to application software, such as some examples of the cardiopulmonary function analyzer 112. These platform services may include inter-process and network communication, file system management and standard database manipulation. One or more of many operating systems may be used, and examples are not limited to any particular operating system or operating system characteristic. For instance, in some examples, the processor 118 may be configured to execute a non-real time operating system, such as BSD or GNU/Linux.

As illustrated in FIG. 1, the cardiopulmonary function analyzer 112, the acoustic signal processing component 124, the electrode signal processing component 126, and the motion signal processing component 128 may be implemented using hardware or a combination of hardware and software. For instance, in one example, the cardiopulmonary function analyzer 112, the acoustic signal processing component 124, the electrode signal processing component 126, and the motion signal processing component 128 are implemented as software components that are stored within the data storage 104 and executed by the processor 118. In this example, the instructions included in the cardiopulmonary function analyzer 112, the acoustic signal processing component 124, the electrode signal processing component 126, and the motion signal processing component 128 program the processor 118 to analyze the cardiopulmonary function of a subject. In some examples, cardiopulmonary function analyzer 112, the acoustic signal processing component 124, the electrode signal processing component 126, and the motion signal processing component 128 may be application-specific integrated circuits (ASICs) that are coupled to the processor 118 and tailored to analyze the cardiopulmonary function of a subject. Thus, examples of the cardiopulmonary function analyzer 112, the acoustic signal processing component 124, the electrode signal processing component 126, and the motion signal processing component 128 are not limited to a particular hardware or software implementation.

In some examples, the components disclosed herein, such as the cardiopulmonary function analyzer 112, the acoustic signal processing component 124, the electrode signal processing component 126, and the motion signal processing component 128 may read parameters that affect the functions performed by the components. These parameters may be physically stored in any form of suitable memory including volatile memory, such as RAM, or nonvolatile memory, such as a flash memory or magnetic hard drive. In addition, the parameters may be logically stored in a propriety data structure, such as a database or file defined by a user mode application, or in a commonly shared data structure, such as an application registry that is defined by an operating system. In addition, some examples provide for both system and user interfaces, as may be implemented using the user interface 108, that allow external entities to modify the parameters and thereby configure the behavior of the components.

The data storage 104 includes a computer readable and writeable nonvolatile data storage medium configured to store non-transitory instructions and data. In addition, the data storage 104 includes processor memory that stores data during operation of the processor 118. In some examples, the processor memory includes a relatively high performance, volatile, random access memory such as dynamic random access memory (DRAM), static memory (SRAM) or synchronous DRAM. However, the processor memory may include any device for storing data, such as a non-volatile memory, with sufficient throughput and storage capacity to support the functions described herein. According to several examples, the processor 118 causes data to be read from the nonvolatile data storage medium into the processor memory prior to processing the data. In these examples, the processor 118 copies the data from the processor memory to the non-volatile storage medium after processing is complete. A variety of components may manage data movement between the non-volatile storage medium and the processor memory and examples are not limited to particular data management components. Further, examples are not limited to a particular memory, memory system, or data storage system.

The instructions stored on the data storage 104 may include executable programs or other code that can be executed by the processor 118. The instructions may be persistently stored as encoded signals, and the instructions may cause the processor 118 to perform the functions described herein. The data storage 104 also may include information that is recorded, on or in, the medium, and this information may be processed by the processor 118 during execution of instructions. The medium may, for example, be optical disk, magnetic disk or flash memory, among others, and may be permanently affixed to, or removable from, the medical device controller 102.

In some examples, the cardiopulmonary data 117 includes cardiopulmonary data detected, identified, and stored by the cardiopulmonary function analyzer 112. More particularly, according to the illustrated example, the cardiopulmonary data 117 includes information descriptive of cardiac function and respiratory function. For example, the cardiopulmonary data 117 may include data such as ECG signal data, interpretations of the ECG signal data (e.g., heartbeats), analog heart sounds, analog breath sounds, analog motion data, acoustic signals, electrode signals, motion signals, processed motion data, processed acoustic data, and processed electrode data.

As illustrated in FIG. 1, the cardiopulmonary function analyzer 112 and the cardiopulmonary data 117 are separate components. However, in some examples, the cardiopulmonary function analyzer 112 and the cardiopulmonary data 117 may be combined into a single component or re-organized so that a portion of the data included in the cardiopulmonary function analyzer 112, such as executable code that causes the processor 118 to analyze enhanced cardiopulmonary data, resides in the cardiopulmonary data 117, or vice versa. Such variations in these and the other components illustrated in FIG. 1 are intended to be within the scope of the examples disclosed herein.

The cardiopulmonary data 117 may be stored in any logical construction capable of storing information on a computer readable medium including, among other structures, flat files, indexed files, hierarchical databases, relational databases or object oriented databases. These data structures may be specifically configured to conserve storage space or increase data exchange performance. In addition, various examples organize the cardiopulmonary data 117 into particularized and, in some cases, unique structures to perform the functions disclosed herein. In these examples, the data structures are sized and arranged to store values for particular types of data, such as integers, floating point numbers, character strings, arrays, linked lists, and the like.

As shown in FIG. 1, the medical device controller 102 includes several system interface components 116, 106, and 114. Each of these system interface components is configured to exchange, i.e. send or receive, data with one or more specialized devices that may be located within the housing of the medical device controller 102 or elsewhere. The components used by the interfaces 116, 106, and 114 may include hardware components, software components, or a combination of both. Within each interface, these components physically and logically couple the medical device controller 102 to the specialized devices. This physical and logical coupling enables the medical device controller 102 to communicate with and, in some examples, power or control the operation of the specialized devices. These specialized devices may include physiological sensors, therapy delivery devices, and computer networking devices.

According to various examples, the hardware and software components of the interfaces 116, 106, and 114 implement a variety of coupling and communication techniques. In some examples, the interfaces 116, 106, and 114 use leads, cables or other wired connectors as conduits to exchange data between the medical device controller 102 and specialized devices. In some examples, the interfaces 116, 106, and 114 communicate with specialized devices using wireless technologies such as radio frequency, infrared technology, and body area network (BAN) technology. The software components included in the interfaces 116, 106, and 114 enable the processor 118 to communicate with specialized devices. These software components may include elements such as objects, executable code, and populated data structures. Together, these software components provide software interfaces through which the processor 118 can exchange information with specialized devices. Moreover, in at least some examples where one or more specialized devices communicate using analog signals, the interfaces 116, 106, and 114 further include components configured to convert analog information into digital information, and vice versa, to enable the processor 118 to communicate with specialized devices.

As discussed above, the system interface components 116, 106, and 114 shown in FIG. 1 support different types of specialized devices. For instance, the components of the sensor interface 114 couple the processor 118 to one or more physiological sensors such as a body temperature sensors, respiration monitors, and ECG sensing electrodes, one or more environmental sensors such as atmospheric thermometers, airflow sensors, video sensors, audio sensors, accelerometers, GPS locators, and hygrometers. In these examples, the sensors may include sensors with a relatively low sampling rate, such as wireless sensors. Additionally, in at least one example, the acoustic signal processing component 124, the electrode signal processing component 126, and the motion signal processing component 128 described above with reference to FIG. 1 are integrated into the sensor interface 114.

The components of the therapy delivery interface 116 couple one or more therapy delivery devices, such as capacitors, defibrillator electrode assemblies, pacing electrode assemblies, or mechanical chest compression devices, to the processor 118. It is appreciated that the functionality of the therapy delivery interface 116 may be incorporated into the sensor interface 114 to form a single interface coupled to the processor 118. In addition, the components of the network interface 106 couple the processor 118 to a computer network via a networking device, such as a bridge, router or hub. According to a variety of examples, the network interface 106 supports a variety of standards and protocols, examples of which include USB (via, for example, a dongle to a computer), TCP/IP, Ethernet, Wireless Ethernet, Bluetooth®, ZigBee, M-Bus, CAN-bus, IP, IPV6, UDP, DTN, HTTP, FTP, SNMP, CDMA, NMEA and GSM. It is appreciated that the network interface 106 of medical device controller 102 may enable communication between other medical device controllers within a certain range.

To ensure data transfer is secure, in some examples, the medical device controller 102 can transmit data via the network interface 106 using a variety of security measures including, for example, TLS, SSL, or VPN. In some examples, the network interface 106 includes both a physical interface configured for wireless communication and a physical interface configured for wired communication. According to various examples, the network interface 106 enables communication between the medical device controller 102 and a variety of personal electronic devices including, for example, computer enabled glasses, watches, and earpieces. In these examples, the network interface 106 may connect to and communicate through a body area network.

Thus, the various system interfaces incorporated in the medical device controller 102 allow the device to interoperate with a wide variety of devices in various contexts. For instance, some examples of the medical device controller 102 are configured to perform a process of sending critical events and data to a centralized server via the network interface 106. An illustration of a process in accord with these examples is disclosed in U.S. Pat. No. 6,681,003, titled "DATA COLLECTION AND SYSTEM MANAGEMENT FOR SUBJECT-WORN MEDICAL DEVICES," issued on Jan. 20, 2004, which is hereby incorporated by reference in its entirety.

As illustrated in FIG. 1, the therapy delivery interface 116 and the network interface 106 are optional and may not be included in every example. For instance, a heart rate monitor may employ the medical device controller 102 to issue alarms but may not include a therapy delivery interface 116 to treat cardiopulmonary abnormalities. Similarly, an ambulatory defibrillator may include the medical device controller 102 to provide defibrillation functionality but may not include a network interface 106 where, for example, the ambulatory defibrillator is designed to rely on the user interface 108 to announce alarms.

The user interface 108 shown in FIG. 1 includes a combination of hardware and software components that allow the medical device controller 102 to communicate with an external entity, such as a subject or other user. These components may be configured to receive information from actions such as physical movement, verbal intonation or thought processes. In addition, the components of the user interface 108 can provide information to external entities. Examples of the components that may be employed within the user interface 108 include keyboards, mouse devices, trackballs, microphones, electrodes, touch screens, printing devices, display screens, and speakers. In some examples, the electrodes include an illuminating element, such as an LED. In some examples, the printing devices include printers capable of rendering visual or tactile (Braille) output.

Other examples may include a variety of features not shown in FIG. 1. For example, although the accelerometer/acoustic sensor 122 and the electrode 120 are shown in FIG. 1 as discrete sensors, some examples may integrate the accelerometer/acoustic sensor 122 and the electrode 120 into a single assembly. In other examples, the accelerometer/acoustic sensor 122 is integrated within a therapy electrode assembly. One such arrangement is described further in U.S. Patent Application Publication No. 2015/0005588, titled "THERAPEUTIC DEVICE INCLUDING ACOUSTIC SENSOR," published Jan. 1, 2015, which is hereby incorporated herein by reference in its entirety. In other examples, the accelerometer/acoustic sensor 122 is integrated within a garment such as the garment described further below with reference to FIG. 2. For instance, the accelerometer/acoustic sensor 122 may be integrated within a belt, vest, or harness, such as the harness 210 or the belt 250. Thus the examples disclosed herein are not limited to a particular number or arrangement of accelerometer/acoustic sensors or electrodes.

Example Ambulatory Medical Device

In some examples, the medical device 100 described above with reference to FIG. 1 is a wearable defibrillator that includes a garment (e.g., a vest or belt) that is worn by the subject. FIG. 2 illustrates a wearable defibrillator 200 in accord with these examples. In at least one example, the wearable defibrillator 200 may be a LifeVest® wearable cardioverter defibrillator available from ZOLL Medical Corporation of Chelmsford, Mass. The wearable defibrillator 200 monitors the subject's ECG with sensing electrodes, monitors the subject heart sounds with acoustic sensors, detects life-threatening arrhythmias, records events of interest, and delivers therapy in the form of one or more pacing pulses or a defibrillating shock through the therapy electrodes if treatment is necessary. As shown in FIG. 2, the wearable defibrillator 200 includes a harness 210 having a pair of shoulder straps and a belt that is worn about the torso of a subject. The wearable defibrillator 200 includes a plurality of ECG sensing electrodes 120 that are attached to the harness 210 at various positions about the subject's body and electrically coupled to the sensor interface 114 of the medical device controller 102 via a connection pod 220. The plurality of ECG sensing electrodes 120 are coupled to the medical device controller 102 to monitor the cardiac function of the subject and generally include an anterior/posterior pair of ECG sensing electrodes and a side/side pair of ECG sensing electrodes. The plurality of ECG sensing electrodes 120 may incorporate any electrode system, including conventional stick-on adhesive electrodes, dry-sensing capacitive ECG electrodes, radio transparent electrodes, segmented electrodes, or one or more long term wear electrodes that are configured to be continuously worn by a subject for extended periods (e.g., 3 or more days). One example of such a long term wear electrode is described in U.S. Patent Application Publication No. 2013/0325096, titled "LONG TERM WEAR MULTIFUNCTION BIOMEDICAL ELECTRODE," published Dec. 5, 2013, which is hereby incorporated herein by reference in its entirety. Additional ECG sensing electrodes may be provided, and the plurality of ECG sensing electrodes 120 may be disposed at various locations about the subject's body.

The wearable defibrillator 200 also includes one or more accelerometer/acoustic sensors 122 that are attached to a belt 250 of the harness 210 at various positions about the subject's body and electrically coupled to the sensor interface 114 of the medical device controller 102 via the connection pod 220. The one or more accelerometer/acoustic sensors 122 are coupled to the medical device controller 102 to monitor the cardiopulmonary function of the subject and generally positioned on the surface of a subject's body in the precordial area.

Figure 6:
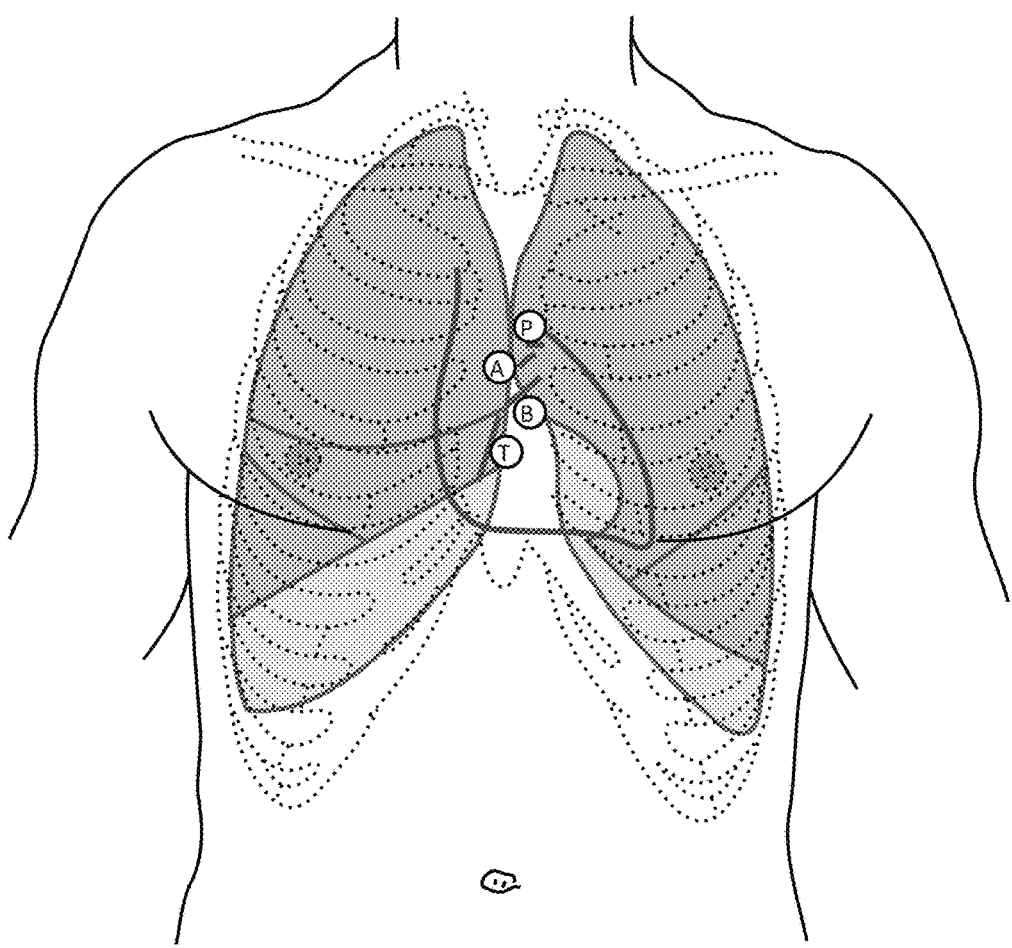
FIG. 6 is an illustration of potential locations for accelerometers/acoustic sensors on the body of a subject.

FIG. 6 illustrates several potential example locations, labeled P, A, B, and T where accelerometer/acoustic sensors 122 can be placed. In one example, the accelerometer/acoustic sensors 122 are positioned near the third intercostal parasternal area. Additionally, table 1 lists primary surface anatomy locations where the accelerometer/acoustic sensors 122 are positioned to detect various cardiac features and anomalies according to some examples.

TABLE 1

| Primary Auscultation Location | Anomaly or Feature |
| --- | --- |
| Second intercostal space at right sternal border | Aortic Value |
| Second intercostal space at left sternal border | Pulmonary Value |
| Third intercostal space at left sternal border | Erb's Point |
| Fourth or fifth intercostal spaces at the left sternal border | Tricuspid Value |
| Fifth intercostal space at midclavicular line | Mitral Value |

In some examples, the accelerometer/acoustic sensors 122 are positioned at secondary posterior locations that correspond to the anterior positions described above. For instance, the accelerometer/acoustic sensors 122 may be positioned at locations near the scapula such as the posterior auxiliary line (V7), midscapular location (V8), or paraspinal location (V9). In one example, the accelerometer/acoustic sensors 122 are positioned at a secondary surface location proximal to the atria.

Figure 2:
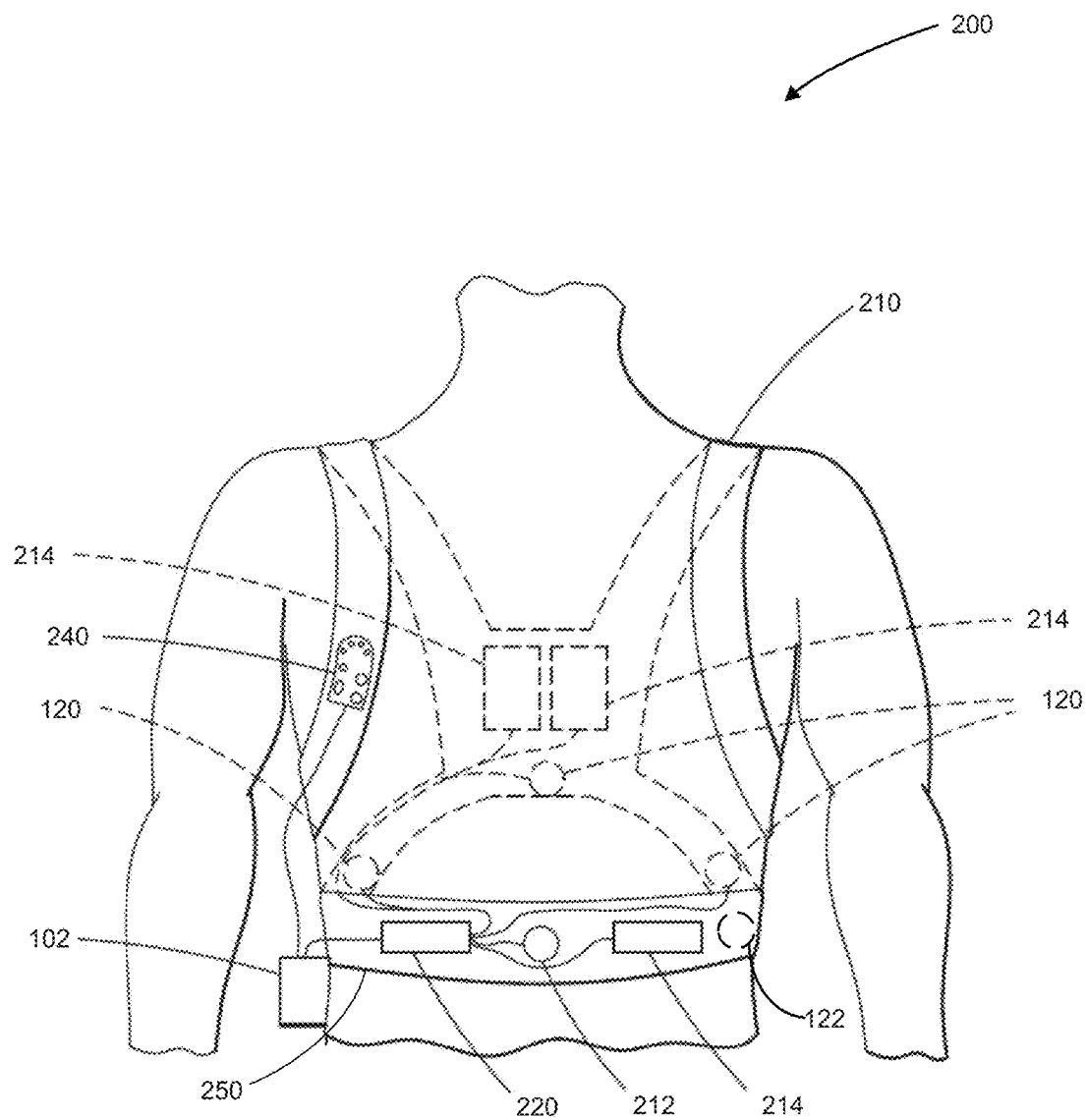
FIG. 2 is an illustration of one example of an ambulatory medical device.

Although not shown is FIG. 2, the wearable defibrillator 200 may include additional sensors, other than the plurality of ECG sensing electrodes 120, capable of monitoring the physiological condition or activity of the subject. For example, sensors capable of measuring blood pressure (via, for example, video blood pressure detection), heart rate, heart sounds, thoracic impedance, pulse oxygen level (via, for example, reflectance-based pulse oximetry to determine oxygen concentration), respiration rate, and the activity level of the subject may also be provided.

The wearable defibrillator 200 also includes a plurality of therapy electrodes 214 that are electrically coupled to the medical device controller 102 via the connection pod 220 and which are configured to deliver one or more therapeutic defibrillating shocks to the body of the subject, if it is determined that such treatment is warranted. Each therapy electrode of the plurality of therapy electrodes may be housed in a therapy electrode assembly that further includes conductive gel disposed within one or more reservoirs. Prior to delivering therapy, the therapy electrode assembly may dispense the conductive gel to improve conductivity between the therapy electrode and the body of the subject. The connection pod 220 electrically couples the plurality of ECG sensing electrodes 120 and the plurality of therapy electrodes 214 to the therapy delivery interface 116 of the medical device controller 102, and may include electronic circuitry configured for this purpose. The connection pod 220 may also include other electronic circuitry, such as a motion sensor or accelerometer through which subject activity may be monitored.

As shown in FIG. 2, the wearable defibrillator 200 also includes a user interface pod 240 that is electrically coupled to, or integrated in with, the user interface 108 of the medical device controller 102. The user interface pod 240 can be attached to the subject's clothing or to the harness 210, for example, via a clip (not shown) that is attached to a portion of the interface pod 240. In some examples, the user interface pod 240 may simply be held in a person's hand. In some examples, the user interface pod 240 may communicate wirelessly with the user interface 108 of the medical device controller 102, for example, using a Bluetooth®, Wireless USB, ZigBee, Wireless Ethernet, GSM, or other type of communication interface.

The user interface pod 240 includes a number of buttons by which the subject, or a bystander can communicate with the medical device controller 102, and a speaker by which the medical device controller 102 may communicate with the subject or the bystander. For example, where the medical device controller 102 determines that the subject is experiencing a cardiac arrhythmia, the medical device controller 102 may issue an audible alarm via a speaker on the medical device controller 102 or the user interface pod 240 alerting the subject and any bystanders to the subject's medical condition. The medical device controller 102 may also instruct the subject to press and hold one or more buttons on the user interface 108 of the medical device controller 102 or on the user interface pod 240 to indicate that the subject is conscious, thereby instructing the medical device controller 102 to withhold the delivery of one or more therapeutic defibrillating shocks. If the subject does not respond, the device may infer that the subject is unconscious, and proceed with the treatment sequence, culminating in the delivery of one or more defibrillating shocks to the body of the subject.

Figure 3A:
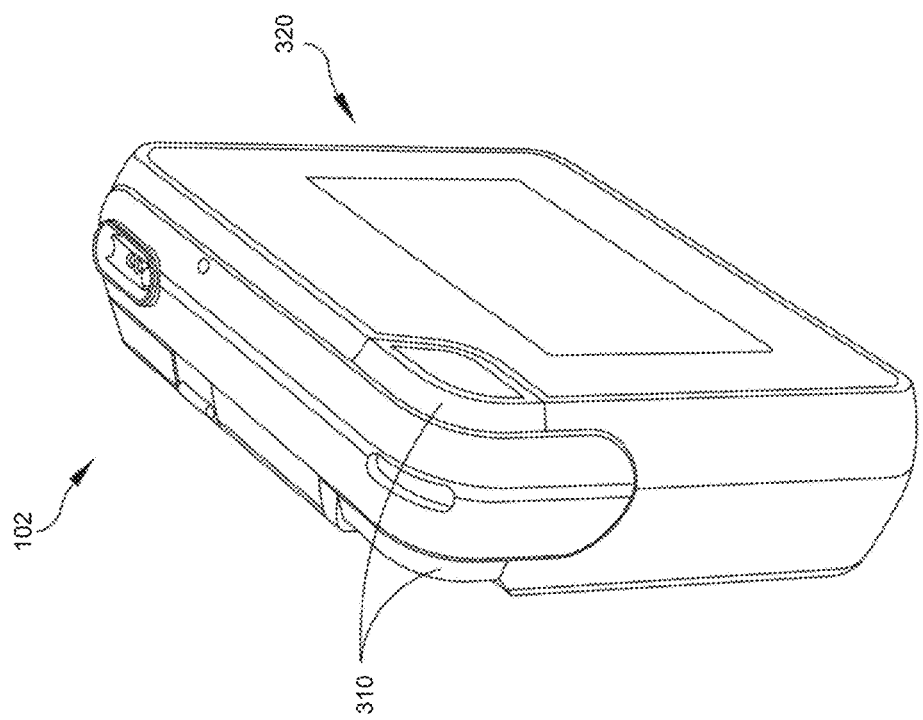
FIGS. 3A-B are illustrations of one example of a medical device controller for an ambulatory medical device.
Figure 3B:
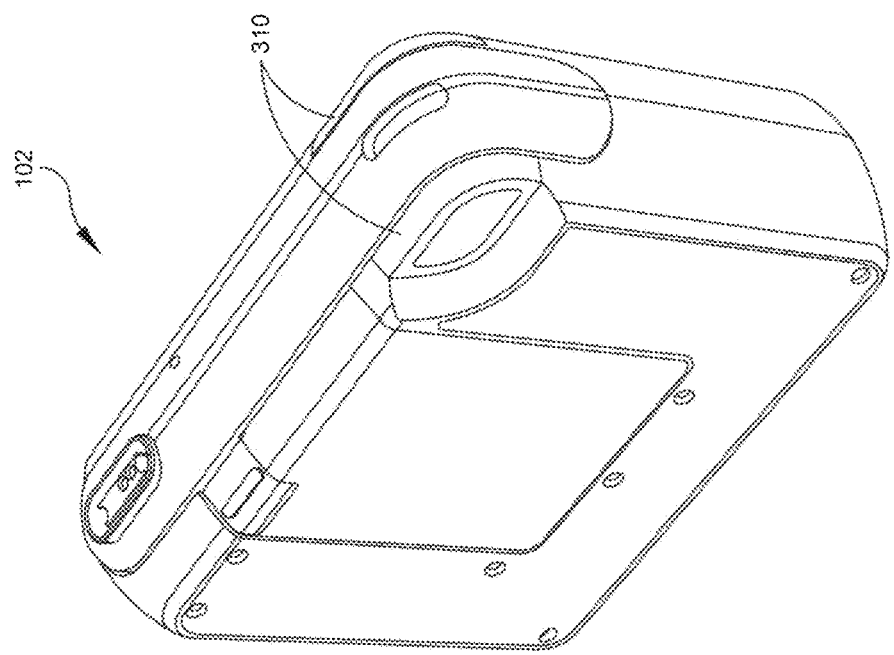

In one example, the functionality of the user interface pod 240 is integrated into the housing of the medical device controller 102. FIGS. 3A-B illustrate such an example of the medical device controller 102. The medical device controller 102 includes two response buttons 310 on opposing sides of the housing of the medical device controller 102. As shown in FIGS. 3A-B, the response buttons 310 are recessed to reduce the likelihood of accidental activation (e.g., a subject falling on the response button). The medical device controller 102 also includes, in this example, a display screen 320 and a speaker to enable the communication of audible and visual stimuli to the subject. It is appreciated that the response buttons 310 do not have to be placed on opposing sides of the housing as illustrated in FIGS. 3A-B. The response buttons, for example, may be located adjacent to each other in the housing the medical device controller 102. The adjacent placement of the response buttons may make it easier for individuals with smaller hands or less dexterity to engage the response buttons.

Example Automated Medical Device

In some examples, the medical device 100 described above with reference to FIG. 1 is an automated external medical device (AED). AEDs are small portable defibrillators that are capable of monitoring cardiac rhythms, determining when a defibrillating shock is necessary, and administering the defibrillating shock either automatically, or under the control of a trained rescuer (e.g., an EMT or other medically training personnel). The AED, in addition, may be configured to provide counseling to an operator as to how to perform cardiac resuscitation (CPR). FIG. 4 illustrates an AED 400. The AED 400 may be, for example, an AED Plus® automated external defibrillator available from ZOLL Medical Corporation of Chelmsford, Mass. As shown, the AED 400 includes a medical device controller 102 and an electrode assembly 402.

The electrode assembly 402 includes one or more sensing electrodes 120 (e.g., ECG sensors), one or more acoustic sensors 122, one or more therapy electrodes 404 (e.g., defibrillation pads), a connector 406, wiring 408 electrically coupling the connector 406 to the one or more sensing electrodes 120, the one or more acoustic sensors, and the one or more therapy electrodes 404. As shown in FIG. 4, the connector is configured to couple the electrode assembly 402 to the medical device controller 102 and, more specifically, the one or more sensing electrodes 120 and the one or more acoustic sensors 122 to the sensor interface 114 and the one or more therapy electrodes to the therapy delivery interface 116.

The medical device controller 102 of the AED 400 is configured to detect the cardiac rhythm of the subject using ECG and heart sounds data and provide pacing and defibrillating shocks to the subject as appropriate. This process is similar to the process described with regard to medical device controller 102 of the ambulatory medical device 200. The user interface 108 of the AED 400 may include a variety of components configured to communicate with the operator including, but not limited to, a display screen, a speaker, and one or more buttons. In this example, the AED 400 includes a display screen to display notifications to an operator. The notifications may provide instructions to the operator regarding the proper administration of CPR to the subject. The notifications on the display may be accompanied by audible alarms from the speaker to further assist the operator in administering CPR to the subject.

In another example, the medical device controller 102 (and more particularly, the cardiopulmonary function analyzer 112 of FIG. 1) of the AED is configured to utilize processed acoustic data to guide an operator through a CPR procedure. In this example, the cardiopulmonary function analyzer 112 issues step by step instructions to the operator and analyzes processed electrode data, processed acoustic data, and processed motion data representative of heart sounds, breath sounds, and physical movement (e.g., chest compressions) to validate performance of each step by the operator. Further, where performance of a given step is inadequate (e.g., chest compressions are not deep enough), the cardiopulmonary function analyzer 112 may issue additional instructions to help the operator adequately perform the given step.

Anomaly Detection Processes

As described above, various examples implement processes through which a medical device identifies and addresses cardiopulmonary anomalies using enhanced cardiopulmonary data. FIG. 5 illustrates one such identification process 500 that utilizes enhanced cardiopulmonary data to identify cardiopulmonary anomaly.

In act 502, a medical device (e.g., the medical device 100 of FIG. 1) receives acoustic, electrode, and motion signals generated from detectable characteristics of physical activity involving the subject, such as motion of the subject's body and/or the subject's cardiopulmonary function. These signals may be received via one or more electrodes (e.g., the electrode 120 of FIG. 1), one or more acoustic sensors, (e.g., the accelerometer/acoustic sensor 122 of FIG. 1), or one or more motion sensors (e.g., the accelerometer/acoustic sensor 122 of FIG. 1). In act 504, the medical device analyzes the received signals using an acoustic signal processing component (e.g., the acoustic signal processing component 124 of FIG. 1), an electrode signal processing component (e.g., the electrode signal processing component 126 of FIG. 1), a motion signal processing component (e.g., the motion signal processing component 128) and a cardiopulmonary function analyzer (e.g., the cardiopulmonary function analyzer 112 of FIG. 1).

For instance, in some examples of the act 504, the acoustic signal processing component and/or the motion signal processing component receive one or more signals from the one or more acoustic sensors, partition the one or more signals into one or more frequency bands, and provide the partitioned signals to the cardiopulmonary function analyzer for further processing. In some examples, the frequency bands correspond to signals generated by certain subject body movements and/or motion such as chest movements during patient breathing (e.g., frequencies less than 3 hertz), chest compressions being performed on the subject (e.g., frequencies between 3 and 20 hertz), heart sounds of the subject (e.g., frequencies between 20 hertz and 150 hertz), and breath sounds of the subject (e.g., frequencies between 300 to 1200 hertz).

The frequency bands recited are approximate and may vary as needed to supply the cardiopulmonary function analyzer with frequency domain information required to infer information regarding subject activity. For example, in one implementation, an estimate of motion may be separated from an estimate of acoustic sounds by partitioning the frequency band into low frequency (e.g., less than 10 hertz may be classified as indicative of patient motion such as breathing movements and/or chest compressions) and high frequency (e.g., greater than 10 hertz, may be classified as indicative as patient acoustic sounds).

In act 506, the cardiopulmonary function analyzer determines whether the subject's cardiopulmonary activity is normal. In some examples, the cardiopulmonary function analyzer determines that the subject's cardiopulmonary activity is normal by analyzing processed electrode data and processed acoustic data covering the same cardiac cycle. More specifically, in some examples, the cardiopulmonary function analyzer compares processed electrode data to preconfigured benchmark data for the subject. This preconfigured benchmark data may include, for example, metrics such as heart rate, QRS duration, QRS axis, PR interval, QT interval, etc. In these examples, the cardiopulmonary function analyzer also, within the act 506, compares processed acoustic data to preconfigured benchmark data that may include, for example, EMAT, LVST, LDPT, and % EMAT. Where the processed electrode data and processed acoustic data substantially match the preconfigured benchmark data, the cardiopulmonary function analyzer determines that the subject's cardiopulmonary activity is normal.

If the subject's cardiopulmonary activity is normal, the process 500 ends. In the event of a detected anomaly, the cardiopulmonary function analyzer attempts to identify and verify an anomaly in act 508. For instance, in some examples of the act 508, the cardiopulmonary function analyzer attempts to identify and verify VT (as distinct from SVT) as follows. First, the cardiopulmonary function analyzer detects a pattern within processed electrode data that indicates whether a subject is experiencing VT. For example, VT can manifest as high frequency ventricular pulses (e.g., more than 100 bpm, or in a range of 110-250 bpm). The processed electrode data may indicate one or more of a non-sustained VT (e.g., a VT that is less than 30 seconds duration), a sustained VT, a monomorphic VT (ventricular beats having similar or same configuration), a polymorphic VT (ventricular beats having changing configurations), or a biphasic VT (a VT having a QRS complex that changes from beat to beat). In some cases, VT can originate from an area that suffered a previous injury (e.g., an earlier myocardial infarction site). As such, the cardiopulmonary function analyzer can consider a source of the VT and correlate the information with the subject's history. To verify a VT episode detected in the processed electrode data, the cardiopulmonary function analyzer can analyze the processed acoustic data covering the same cardiac cycle as the processed electrode data. For example, VT can have a lower S1 intensity or higher S1 variability than supraventricular rhythm (2.63±1.78 mV vs. 4.70±5.03 mV and 0.45±0.24 vs. 0.21±0.11, respectively). In this regard, the cardiopulmonary function analyzer can determine whether S1 intensity is below a value of a first configurable parameter. In some examples, the cardiopulmonary analyzer can also determine whether S1 beat-to-beat variability is above a value of a second configurable parameter. Where the S1 intensity is below the value of the first configurable parameter or the S1 variability is above the value of the second configurable parameter, the cardiopulmonary function analyzer may conclude that the detected VT episode is actual and verifies the VT episode. Otherwise, the cardiopulmonary function analyzer may conclude the detected VT episode is unverified (e.g., the anomaly may be SVT). For example, the first configuration parameter for the S1 intensity threshold can be configured to be in a range defined by 4.70 mV+/−5.03 mV. For example, the second configurable parameter for the S1 variability threshold can be in a range defined by 0.21+/−0.11. It should be understood that other values outside these ranges are possible, and are not to be limited to the ranges described here.

In some examples of the act 508, the cardiopulmonary function analyzer can identify PEA as follows. For example, the cardiopulmonary function analyzer analyzes processed electrode data and detects a pattern within the processed electrode data that indicates a subject is experiencing PEA. For example, the cardiopulmonary function analyzer may detect that the QRS duration of the subject is greater than the value of a configurable parameter (e.g., 180 milliseconds). To verify this detected PEA, the cardiopulmonary function analyzer can analyze processed acoustic data covering the same cardiac cycle as the processed electrode data. More specifically, the cardiopulmonary function analyzer can determine, for example, that the EMAT within the cardiac cycle is greater than the value of a configurable parameter (e.g., 150 milliseconds), or that the processed acoustic data includes no heart sounds. Where the cardiopulmonary function analyzer identifies either of these patterns in the processed acoustic data, the cardiopulmonary function analyzer can confirm the detected PEA diagnosis and verifies the PEA episode. Otherwise, the cardiopulmonary function analyzer can conclude that the detected PEA is unverified.

In some examples of the act 508, the cardiopulmonary function analyzer can identify asystole as follows. For example, the cardiopulmonary function analyzer analyzes processed electrode data and detects a pattern within the processed electrode data that indicates a subject is experiencing asystole. For example, asystole can manifest as a flatline in ECG data. To verify this detected asystole, the cardiopulmonary function analyzer can analyze processed acoustic data covering the same cardiac cycle as the processed electrode data. For example, the cardiopulmonary function analyzer can determine whether the processed acoustic data includes no heart sounds. If no heart sounds are detected, the cardiopulmonary function analyzer can confirm that the detected asystole episode is a correct diagnosis and verifies the asystole episode. Otherwise, the cardiopulmonary function analyzer can identify the detected asystole as unverified. In some implementations, the cardiopulmonary function analyzer can use other information such as, motion data (e.g., chest rise and fall), respiratory movements, or respiratory sounds to confirm the asystole diagnosis.

In some examples of the act 508, the cardiopulmonary function analyzer can identify pseudo-PEA as follows. For example, the cardiopulmonary function analyzer can analyze processed electrode data and detect a pattern within processed electrode data that indicates a subject is experiencing pseudo-PEA. For example, the cardiopulmonary function analyzer may detect that the QRS duration of the subject is within a range associated with pseudo-PEA (e.g., 120-180 milliseconds). This range may be specified by one or more configurable parameters. To verify this detected pseudo-PEA, the cardiopulmonary function analyzer can analyze processed acoustic data covering the same cardiac cycle as the processed electrode data. More specifically, the cardiopulmonary function analyzer can determine, for example, that the EMAT within the cardiac cycle is within a range specified by one or more configurable parameters (e.g., 90-150 milliseconds). Where the cardiopulmonary function analyzer identifies this pattern in the processed acoustic data, the cardiopulmonary function analyzer can confirm the detected pseudo-PEA diagnosis and verify the pseudo-PEA episode. Otherwise, the cardiopulmonary function analyzer can conclude that the detected pseudo-PEA is unverified.

In some examples of the act 508, the cardiopulmonary function analyzer can identify degenerative bradycardia/pseudo-PEA/PEA where the cardiopulmonary function analyzer detects a gradually degrading EMAT within processed acoustic data over a period of time having a duration specified by a configurable parameter. In at least one example, the period of time is a configurable parameter with a value set between 10 minutes and 1 hour. Where the EMAT degrades at a rate specified by a configurable parameter, the cardiopulmonary function analyzer verifies the degenerative bradycardia/pseudo-PEA/PEA episode.

In some examples of the act 508, the cardiopulmonary function analyzer can identify respiratory arrest as follows. For example, the cardiopulmonary function analyzer can analyze EMAT data within processed acoustic data and detect a gradually degrading EMAT over a period of time. For example, such a period of time can have a duration specified by a configurable parameter. Next the cardiopulmonary function analyzer can determine whether, within the period of time with a gradually degrading EMAT, a gradually increasing time span between the apex of chest rise and the nadir of chest fall is being exhibited by the subject. In some examples, the cardiopulmonary function analyzer determines the time span between the apex of the chest rise and the nadir of chest fall by analyzing low frequency (e.g., 0.1 Hz) and high frequency breath sounds. Where the time span transgresses a threshold value defined by a configurable parameter (and thus indicates labored breathing), the cardiopulmonary function analyzer can confirm the detected respiratory arrest diagnosis, and thereby verify the detected respiratory arrest.

In some examples of the act 508, the cardiopulmonary function analyzer can identifies sleep apnea by analyzing the strength of the S3 sound of a subject. Where the cardiopulmonary analyzer determines that the S3 sound has strength greater than a value specified by a configurable parameter (e.g., 5), the cardiopulmonary function analyzer can confirm that sleep apnea diagnosis and an episode of sleep apnea is verified.

In some examples of the act 508, the cardiopulmonary function analyzer can identify ECG sensing electrode falloff in some situations (e.g., when the processed electrode data indicates that the subject is undergoing asystole). For example, consider a scenario in which the cardiopulmonary function analyzer analyzes processed electrode data and detects a pattern within the processed electrode data that indicates a subject is experiencing asystole. To verify this detected asystole episode, the cardiopulmonary function analyzer can analyze the processed acoustic data from the same time period as the time period in which the cardiopulmonary function analyzer analyzes the processed electrode data. If the processed acoustic data includes normal heart sounds, the cardiopulmonary function analyzer can conclude that the detected asystole episode is unverified. The cardiopulmonary function analyzer can then alert the subject, a support person, or other external entity, about a potential electrode falloff, rather than initiate a routine relating to treating the asystole condition.

In some examples, the cardiopulmonary function analyzer can further analyze processed motion data from a same time period as a time period in which the cardiopulmonary function analyzer analyzes the processed electrode data. Where the processed motion data indicates a subject is displaying a level of activity greater than a value of a configurable parameter, the cardiopulmonary function analyzer can conclude that the detected asystole episode is actually a verified electrode falloff.

If, within the act 508, the cardiopulmonary function analyzer identifies and verifies an anomaly, the cardiopulmonary function analyzer proceeds to act 510. Otherwise, the cardiopulmonary function analyzer proceeds to the act 514. In the act 514 the cardiopulmonary function analyzer stores a record of the detected abnormal cardiopulmonary activity, issues a notification indicating the abnormal activity to an external entity (e.g., user or remote system), and returns to the act 502.

In act 510, the cardiopulmonary function analyzer identifies a routine associated with the identified anomaly by, for example, referring to a configurable cross-reference parameter stored in a data storage (e.g., the data storage 104 of FIG. 1) that associates each detectable anomaly with a routine to address the anomaly. Next, within act 512, the cardiopulmonary function analyzer addresses the anomaly by executing the identified routine. These routines may address anomalies by executing a variety of processes. In one example of the act 512, the cardiopulmonary function analyzer addresses verified VT, verified asystole, and verified PEA by executing a defibrillation sequence, culminating in the delivery of one or more defibrillating shocks to the body of the subject. In some examples of the act 512, the cardiopulmonary function analyzer addresses ECG sensor falloff by communicating an alarm to an external entity, such as a subject, a caregiver, a technician, or a remote computer system. In at least one example of the act 512, the cardiopulmonary function analyzer addresses verified bradycardia and verified pseudo-PEA by executing a pacing routine. In some examples of the act 512, the cardiopulmonary function analyzer addresses verified respiratory arrest by communicating an alarm to the subject or a caregiver. In some examples the alarm may include a mild shock or high volume audio signal to stir the subject. In some examples of the act 512, the cardiopulmonary function analyzer addresses verified or unverified SVT by communicating an alarm to a caregiver. Examples of the types of alarms communicated in the act 512 are described in U.S. Patent Application Publication No. 2012/0293323, titled "SYSTEM AND METHOD FOR ADAPTING ALARMS IN A WEARABLE MEDICAL DEVICE," filed Mar. 23, 2012, which is hereby incorporated herein by reference in its entirety.

After execution of the act 512, the process 500 ends. The process 500 may execute repeatedly during operation of the medical device to monitor and potentially treat the subject as needed.

Process 500 depicts one particular sequence of acts in a particular example. The acts included in this process may be performed by, or using, one or more computer systems specially configured as discussed herein. Some acts are optional and, as such, may be omitted in accord with one or more examples. Additionally, the order of acts can be altered, or other acts can be added, without departing from the scope of the systems and methods discussed herein. Furthermore, as discussed above, in at least one example, the acts are performed on a particular, specially configured machine, namely a medical device configured according to the examples disclosed herein.

Having thus described several aspects of at least one example of this disclosure, it is to be appreciated various alterations, modifications, and improvements will readily occur to those skilled in the art. Such alterations, modifications, and improvements are intended to be part of this disclosure, and are intended to be within the scope of the disclosure. Accordingly, the foregoing description and drawings are by way of example only.

The invention claimed is:

1. A medical device comprising:
   at least one electrocardiogram (ECG) electrode;
   at least one acoustic sensor comprising at least one accelerometer; and
   at least one processor coupled with the at least one acoustic sensor and the at least one ECG electrode and configured
      to receive at least one signal from the at least one accelerometer,
      to partition the at least one signal into at least one acoustic signal comprising frequencies greater than approximately 10 hertz and at least one motion signal comprising frequencies less than approximately 10 hertz,
      to receive at least one electrical signal from the at least one ECG electrode, and
      to detect at least one cardiopulmonary anomaly using the at least one electrical signal and the at least one acoustic signal.

2. The medical device of claim 1, wherein the at least one processor is configured to detect the at least one cardiopulmonary anomaly at least in part by identifying the at least one cardiopulmonary anomaly using the at least one electrical signal and verifying the at least one cardiopulmonary anomaly using the at least one acoustic signal.

3. The medical device of claim 1, further comprising a garment, wherein the at least one ECG electrode and the at least one acoustic sensor are integrated with the garment.

4. The medical device of claim 3, further comprising at least one therapy electrode coupled with the at least one processor, the at least one therapy electrode integrated with the garment.

5. The medical device of claim 1, wherein the at least one acoustic signal comprises at least one of S1, S2, S3, and S4 signals.

6. The medical device of claim 1, wherein the at least one processor is configured to detect the at least one cardiopulmonary anomaly at least in part by calculating, based on the at least one acoustic signal, at least one of electromechanical activation time (EMAT), EMAT as a percentage of cardiac cycle time, systolic dysfunction index, and left ventricular systolic time.

7. The medical device of claim 1, wherein the at least one cardiopulmonary anomaly comprises at least one of supraventricular tachycardia, ventricular tachycardia, pulseless electrical activity, asystole, a heart murmur, sleep apnea, and respiratory failure.

8. The medical device of claim 1, wherein the at least one processor is configured to detect disconnection of the at least one ECG electrode from a patient's skin based on the at least one acoustic signal.

9. The medical device of claim 1, wherein the at least one processor is configured to partition the at least one signal into a first frequency band for subject motion, a second frequency band for chest compression motion, a third frequency band for heart sounds, and a fourth frequency band for breath sounds.

10. The medical device of claim 9, wherein the first frequency band comprises frequencies less than approximately 3 hertz, the second frequency band comprises frequencies between approximately 3 and 20 hertz, the third frequency band comprises frequencies between approximately 20 hertz and 150 hertz, and the fourth frequency band comprises frequencies between approximately 300 to 1200 hertz.

11. The medical device of claim 1, wherein the medical device comprises an ambulatory medical device.

12. A method of monitoring a subject using a wearable defibrillator comprising at least one electrocardiogram (ECG) electrode and at least one acoustic sensor comprising at least one accelerometer, the method comprising:
receiving at least one signal from the at least one accelerometer;
partitioning the at least one signal into at least one acoustic signal comprising frequencies greater than approximately 10 hertz and at least one motion signal comprising frequencies less than approximately 10 hertz;
receiving at least one electrical signal from the at least one ECG electrode; and
detecting at least one cardiopulmonary anomaly using the at least one electrical signal and the at least one acoustic signal.

13. The method of claim 12, wherein partitioning the at least one signal comprises partitioning the at least one signal into at least one of S1, S2, S3, and S4 signals.

14. The method of claim 12, wherein detecting the at least one cardiopulmonary anomaly comprises calculating, based on the at least one acoustic signal, at least one of electromechanical activation time (EMAT), EMAT as a percentage of cardiac cycle time, systolic dysfunction index, and left ventricular systolic time.

15. The method of claim 12, wherein detecting the at least one cardiopulmonary anomaly comprises detecting at least one of supraventricular tachycardia, ventricular tachycardia, pulseless electrical activity, asystole, a heart murmur, sleep apnea, and respiratory failure.

16. The method of claim 12, further comprising detecting the at least one cardiopulmonary anomaly using the at least one electrical signal, the at least one acoustic signal, and the at least one motion signal.

17. The method of claim 12, wherein detecting the at least one cardiopulmonary anomaly comprises identifying the at least one cardiopulmonary anomaly using the at least one electrical signal and verifying the at least one cardiopulmonary anomaly using the at least one acoustic signal.

18. A medical device comprising:
at least one electrocardiogram (ECG) electrode;
at least one acoustic sensor comprising at least one accelerometer; and
at least one processor coupled with the at least one acoustic sensor and the at least one ECG electrode and configured
to receive at least one signal from the at least one accelerometer,
to partition the at least one signal into at least one acoustic signal and at least one motion signal,
wherein to partition the at least one signal into the at least one acoustic signal and the at least one motion signal comprises to partition the at least one signal into a first frequency band comprising frequencies less than approximately 3 hertz for subject motion, a second frequency band comprising frequencies between approximately 3 hertz and 20 hertz for chest compression motion, a third frequency band comprising frequencies between approximately 20 hertz and 150 hertz for heart sounds, and a fourth frequency band comprising frequencies between approximately 300 hertz to 1200 hertz for breath sounds,
receive at least one electrical signal from the at least one ECG electrode, and
detect at least one cardiopulmonary anomaly using the at least one electrical signal and the at least one signal.

19. The medical device of claim 18, wherein the at least one processor is configured to detect the at least one cardiopulmonary anomaly at least in part by identifying the at least one cardiopulmonary anomaly using the at least one electrical signal and verifying the at least one cardiopulmonary anomaly using the at least one acoustic signal.

20. The medical device of claim 18, further comprising a garment, wherein the at least one ECG electrode and the at least one acoustic sensor are integrated with the garment.

21. The medical device of claim 20, further comprising at least one therapy electrode coupled with the at least one processor, the at least one therapy electrode integrated with the garment.

22. The medical device of claim 18, wherein the at least one acoustic signal comprises at least one of S1, S2, S3, and S4 signals.

23. The medical device of claim 22, wherein the at least one processor is configured to detect the at least one cardiopulmonary anomaly at least in part by calculating, based on the at least one acoustic signal, at least one of electromechanical activation time (EMAT), EMAT as a percentage of cardiac cycle time, systolic dysfunction index, and left ventricular systolic time.

24. The medical device of claim 18, wherein the at least one cardiopulmonary anomaly comprises at least one of supraventricular tachycardia, ventricular tachycardia, pulseless electrical activity, asystole, a heart murmur, sleep apnea, and respiratory failure.

25. The medical device of claim 18, wherein the at least one processor is configured to detect disconnection of the at least one ECG electrode from a patient's skin based on the at least one acoustic signal.

* * * * *